United States Patent [19]

Böttger et al.

[11] 4,234,252
[45] Nov. 18, 1980

[54] APPARATUS FOR THE SIMULTANEOUS PHOTOMETRIC DETERMINATION OF A PLURALITY OF ELEMENTS IN A LIQUID SAMPLE

[75] Inventors: Klaus Böttger, Oberkochen; Dieter Müller, Königsbronn; Karl-W. Schmekel, Oberkochen; Walter Tausch, Aalen, all of Fed. Rep. of Germany

[73] Assignee: Carl Zeiss-Stiftung, Oberkochen, Fed. Rep. of Germany

[21] Appl. No.: 3,124

[22] Filed: Jan. 12, 1979

[30] Foreign Application Priority Data

Jan. 19, 1978 [DE] Fed. Rep. of Germany ....... 2802147

[51] Int. Cl.³ ............................................. G01N 21/72
[52] U.S. Cl. ..................................... 356/73; 356/315; 356/417
[58] Field of Search ......................... 356/315, 417, 73

[56] References Cited

PUBLICATIONS

Bukreev et al., *Journal of Applied Spectroscopy*, vol. 23, No. 1, Jul. 1975, pp. 888–892.

*Primary Examiner*—F. L. Evans
*Attorney, Agent, or Firm*—Hopgood, Calimafde, Kalil, Blaustein & Lieberman

[57] ABSTRACT

The invention contemplates apparatus for simultaneous photometric observation of a plurality of elements in a liquid sample, wherein a dilute solution of the sample is atomized and fed to an elongate steady flame and wherein light from a hollow-cathode lamp, and containing at least one narrow-band emission line of one of the elements to be determined, is directed through the flame; plural photoelectric receivers, each with an associated filter unique to a line characteristic of a different specific element to be determined, are disposed to respond to light passing through the flame or to light emitted by the flame, as the case may be. The detected outputs of the receivers are fed to a computer for evaluation, the outputs of emission receivers being first electronically processed for the effective removal of "dust flashes" in the flame.

10 Claims, 4 Drawing Figures

APPARATUS FOR THE SIMULTANEOUS PHOTOMETRIC DETERMINATION OF A PLURALITY OF ELEMENTS IN A LIQUID SAMPLE

BACKGROUND OF THE INVENTION

The present invention relates to apparatus for the simultaneous photometric determination of a plurality of elements in a liquid sample, in which apparatus a receiver is associated with each of the elements to be determined and the signals supplied by said receivers are evaluated via a computer.

The liquid sample under examination may, for instance, be a body fluid, such as serum, urine, spinal fluid, etc., the purpose generally being to determine the content of sodium, potassium, calcium and frequently also, magnesium in the sample.

A flame photometer for the simultaneous determination of sodium and potassium in a sample dilution is already known. However, calcium, which is important for diagnosis, and furthermore magnesium, which is important, for instance, for dialysis centers, cannot be determined with the known device.

It is also known to determine the elements sodium, potassium, and calcium one after the other by means of a flame photometer. In this case, however, different dilutions are needed, so that the time required for the measurement, and the amount of sample needed are relatively great. Here again, the measurement of magnesium is not possible, and the determination of calcium is subject to error.

Finally, it is also known to determine sodium and potassium one after the other through flame emission, and calcium and magnesium one after the other through atomic absorption. Aside from the fact that instruments for such determinations are expensive and make high demands on the operator, the time and the quantity of sample required for a measurement of the said elements are rather great.

The foregoing shortcomings are due, in particular, to the fact that so-called comparison elements are necessary, which form an internal standard by means of which it is possible to eliminate variations in measurement values. A comparison element is added to the sample, has the same energy of excitation as the element being analyzed, and is measured simultaneously with the latter in the same section of the flame. For sodium and potassium, lithium is customarily used as the comparison element in emission photometry. For the analysis of calcium by atomic absorption, strontium is suitable as the comparison element; and for the analysis of magnesium, cadmium is suitable.

It is clear that when determining four elements, the time and sample quantity required for a measurement, as well as the equipment expense for the preparation of the sample, are all rather high. Furthermore, undesired or even disturbing effects of the addition of such comparison elements are likely if the necessary measurement conditions are not precisely satisfied.

SUMMARY OF THE INVENTION

The object of the present invention is to provide a device for the simultaneous photometric determination of a plurality of elements in a liquid sample, making it possible to determine four elements in a single sample dilution, using little time and a smaller quantity of sample, and without the use of comparison elements.

This object is achieved in accordance with the presently disclosed preferred form of the invention, by the combination of the following elements whose interaction is necessary in order to achieve the intended purpose:

(a) at least one hollow-cathode lamp whose light contains at least one narrow-band emission line of one of the elements to be determined;

(b) an elongate flame to which diluted sample liquid is fed via an atomizer;

(c) photoelectric receivers arranged laterally of the flame for measurement in emission;

(d) photoelectric receivers arranged behind the flame for measurement of such lamp radiation as penetrates longitudinally through the flame;

(e) narrow-band filters arranged in front of each receiver to limit receiver response, to a line which is characteristic of the specific element to be determined;

(f) means for the electronic removal of "dust flashes" in the flame;

(g) a double-walled stack which surrounds the elongated flame, one side of the stack having openings for entrained passage of outer air in the lower part of the outer wall and in the upper part of the inner wall.

The above-itemized elements a, b, d, e and g together have the result that at least one, and preferably two, elements simultaneously can be measured by atomic absorption. These two elements are preferably calcium and magnesium, the detection of which in atomic absorption is particularly sensitive in the same combination.

The narrow-band filters arranged in front of the receivers are developed in such manner that, in cooperation with the specific-line radiation of the hollow-cathode lamp, they permit passage only of radiation within a very narrow wave-length interval, of for instance 0.003 nm, at the corresponding resonance line of the element to be measured.

Thus, when using a Ca/Mg hollow-cathode lamp, it is possible to measure calcium or magnesium in atomic absorption, calcium being determined at the 422.7 nm line and magnesium at the 285.2 nm line. In atomic-absorption measurement using a very narrow absorption line, spectral disturbances such as, for instance, a disturbance in the determination of calcium as a function of varying sodium content of the matrix, do not occur.

The above-itemized elements b, c, e, f and g together make it possible that at least one, and preferably two, additional elements can be measured in emission simultaneously with the atomic-absorption measurement. These additional elements are preferably sodium and potassium.

Only half of the amount of oxygen necessary for complete combustion is obtained by the flame from the surrounding air. In this connection, the particles of dust present in the outer air also pass into the flame. On their path through the flame the particles of dust, which customarily contain a large amount of sodium and potassium, burn and intensively emit the radiation of these two elements. Since the particles of dust burn rapidly in the flame one speaks of "dust flashes". These flashes cause a photoelectric receiver to produce brief signal pulses which are of many times greater amplitude than the useful signal, so that erroneous measurements can occur, depending on the amount of dust in the entrained air.

These erroneous measurements are avoided in the new device by electronically effectively removing "dust flashes" in the flame, so that the emission measurement of the two elements, sodium and potassium, may take place without interference.

It is advisable to use an automatic flow regulator for the fuel gas, to avoid disturbance-induced variations in the supply of fuel gas, such disturbances being disruptive of the desired, otherwise quiet, nature of the flame.

Despite such regulation, a flickering of the flame can occur, caused by the outer air, which results in varying measured values. In order to avoid such a flickering of the flame both upon absorption measurement and upon emission measurement, it is necessary to make the outer air necessary for complete combustion, available with a sufficiently laminar flow to the flame. This is accomplished by element g of the inventive combination. As a result of the special development of the double-walled stack, the air required for the after-burning is fed preheated, in laminar flow, to the flame, the upper part of the flame being simultaneously supported by this air. The double-walled development of the stack at the same time screens off excessive radiation of heat from the mechanical and electronic units surrounding the stack.

The double-walled stack which surrounds the flame makes it possible to mask out marginal regions of the flame for the emission measurement and to select for the measurement a given portion of the flame in which the element in question burns most quietly. For this purpose, corresponding openings are provided in the double wall of the stack, the orientation and location of said openings being predetermined for optimal measurement angle and for an optimally viewed portion of the flame, for the particular element to be observed in each case.

The new device makes it possible to measure four elements simultaneously with only a single sample solution. The sample solution itself is for this purpose greatly diluted, a dilution of about 1:50 having been found optimum for serum. In order to be able to operate without buffer solution, particularly upon the determination of calcium, and nevertheless to avoid disturbances induced by the presence of a phosphate, the atomizer unit provided in front of the burner is so developed that the aerosol droplets atomized into the flame are as small as possible. In order to permit the simultaneous determination of four elements in a sample solution also over broad measurement ranges it is necessary to effect a correction of the curvature of the calibration curve for each element. The linearizing of the curve can be effected mechanically by cams; however, an electronic solution is more advantageous.

The device in accordance with the invention makes it possible to determine simultaneously the elements sodium, potassium, calcium, and magnesium in serum with a relative standard deviation of less than 1%, in which connection the amount of sample required is small, the preparation of the sample is very simple, and the measurement is reliable and free of error. The apparatus itself is simple and easy to operate.

DESCRIPTION OF AN ILLUSTRATIVE EMBODIMENT

The invention will be described in further detail below with reference to FIGS. 1 to 4 of the accompanying drawings, in which.

Figure 1:
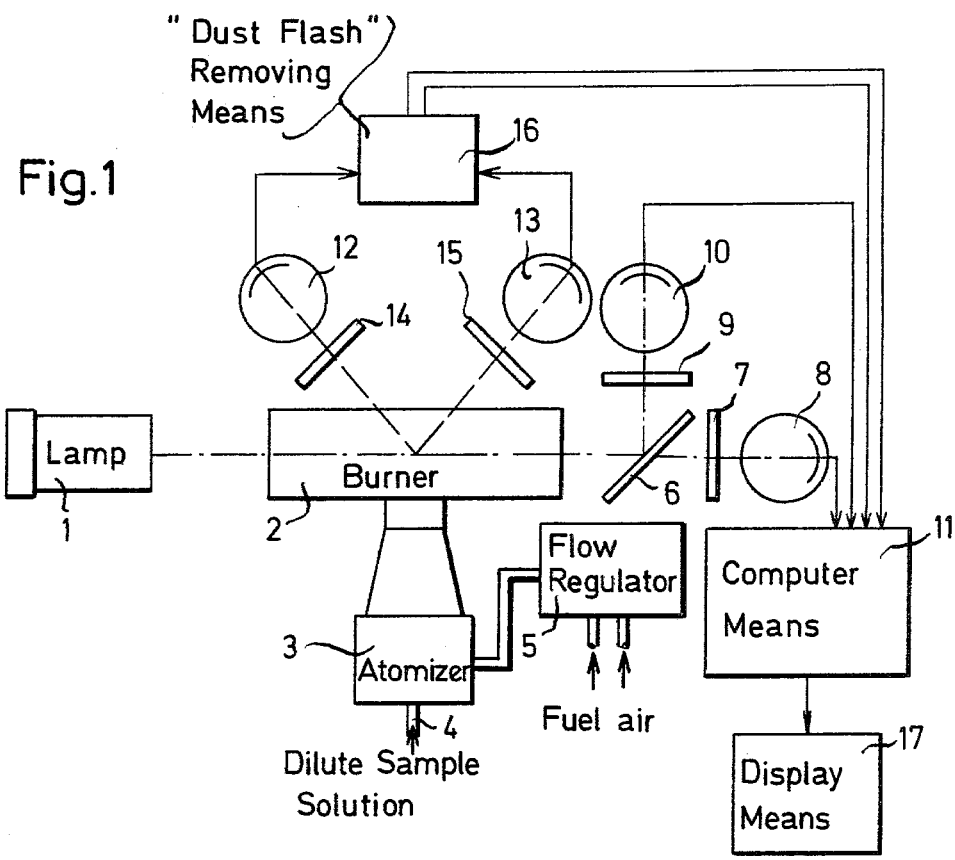
FIG. 1 is a diagram schematically showing a device embodying the invention.

In FIG. 1, a Ca/Mg hollow-cathode lamp 1 emits resonance radiation at 285.2 and 422.7 nm. This radiation passes through an elongate flame in a burner 2, to which sample solution is fed via an atomizer 3, with aerosol droplets as small as possible. The sample solution is fed in final dilution to the atomizer 3 via a hose 4, the diluting being effected, for instance, in a separate dilution unit, not shown here. The fuel gas, an acetylene-air mixture, is fed to the burner 2 via an automatic flow regulator 5.

Radiation emitted by the hollow-cathode lamp 1 passes through the flame and impinges upon a semi-transparent mirror 6; from there it passes via a filter 7 to a receiver 8, and via a filter 9 to a receiver 10. The two filters 7 and 8 are developed as interference filters, the filter 7 passing only the calcium resonance line (422.7 nm) and the filter 9 only the magnesium resonance line (285.2 nm). Signals produced by receivers 8 and 10 are fed to a computer 11.

Two additional receivers 12 and 13 are positioned laterally of the burner 2, to measure radiation emitted by the burner flame.

In front of receiver 12, there is arranged a filter 14 which passes only the sodium line (589 nm), and a filter 15 arranged in front of the receiver 13 passes only the potassium line (766 nm). Signals produced by the receivers 12 and 13 are fed to means 16 for the electronic removal of "dust flashes" in the flame, and they are then also fed to the computer 11.

In the computer 11, the measurement signals are evaluated on the basis of electronically linearized calibration curves for the respective four measured elements, being finally fed to display means 17 which may for example provide the measured values in the form of a print-out.

Figure 2:
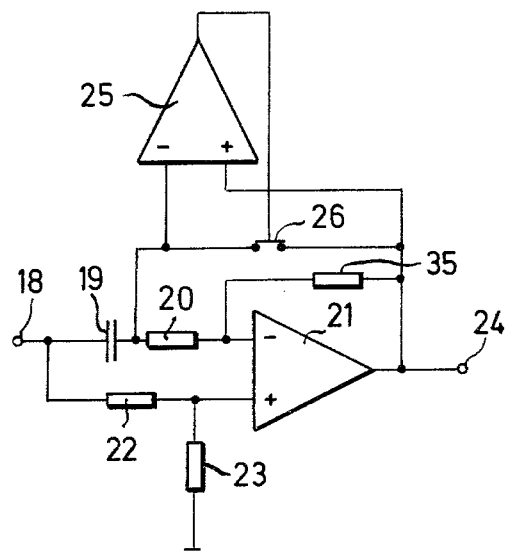
FIG. 2 is a circuit diagram of an arrangement for electronic removal of "dust flashes" in the device of FIG. 1.

Construction of the means 16 is schematically shown in FIG. 2, it being understood that a separate circuit (as in FIG. 2) is preferably provided for each of the outputs of receivers 12–13, although for certain purposes a single circuit (as in FIG. 2) will suffice if the input connection is alternated in its switched connection in alternation to receivers 12–13. The signal produced, say, by the receiver 12, is fed via input 18 to an RC circuit arm, consisting of a capacitor 19 and a resistor 20, and passes thence to one input of an operational amplifier 21. The signal at input 18 passes simultaneously over a resistance divider 22–23 to the other input of the operational amplifier 21. The voltage present at the output 24 of amplifier 21 passes to a negative feedback resistor 35. The division ratio of the resistors 22–23 and 20–35 is approximately the same. Output voltage at 24 is also fed, together with the voltage at the connection of capacitor 19 and resistor 20, to the respective inputs of a comparator 25 whose output is connected with an electronic switch 26, which may, for instance, be a switching transistor. A bias voltage which corresponds approximately to the noise level, and therefore is in the order of magnitude of 10 mV, is present on the comparator 25.

In normal measurement operations, i.e., when no "dust flashes" occur, the capacitor 19 will have become charged to a voltage which is determined by the division ratio of the resistors 22-23 and which therefore corresponds to the output voltage 24. Illustratively, the output voltage at 24 is in the order of magnitude of 4 volts. Upon occurrence of a "dust flash", a positive disturbing voltage appears at the input 18 and is initially present at both inputs of the amplifier 21, i.e., no change occurs at the output 24. During the occurrence of the disturbing voltage, the capacitor 19 has become charged in accordance with the time constant of the RC arm 19-20, so that a negative voltage is present at the upper input of the amplifier 21. This causes a positive change in voltage at the output 24, i.e., the voltages present at the inputs of the comparator 25 differ by more than the bias voltage. At this moment, comparator 25 gives off a signal which closes switch 26 and thus discharges the capacitor 19 down to the bias voltage.

The circuit of FIG. 2 will be seen also to operate upon the occurrence of negative disturbing voltages at input 18.

It is clear from this explanation that "dust flashes" which act as disturbing voltages do not have any effect on the output voltage fed to the computer 11, i.e., the dust flashes are filtered out electronically.

Figure 3:
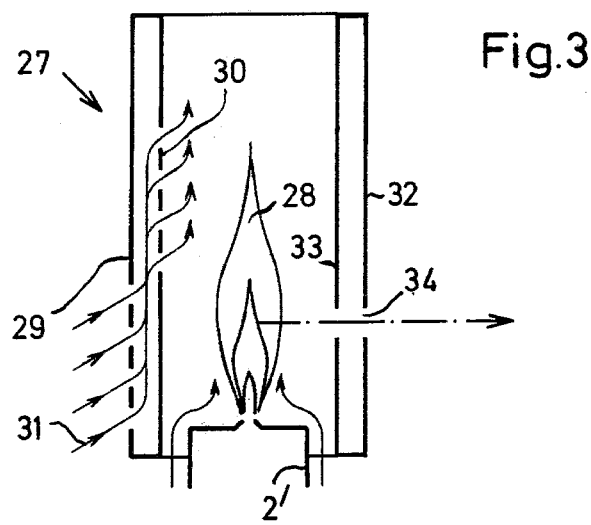
FIG. 3 is a simplified longitudinal section through the double-walled stack which surrounds the flame in the burner forming part of the device of FIG. 1.
Figure 4:
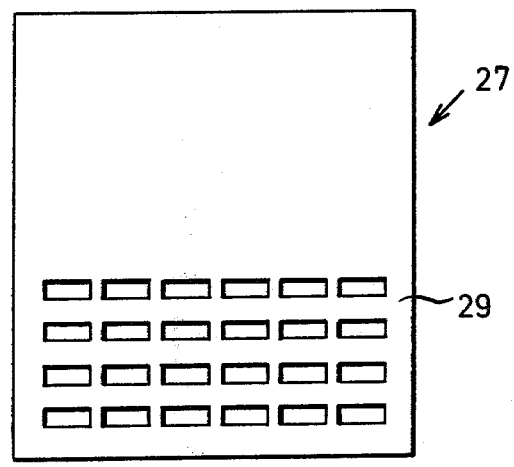
FIG. 4 is a front view of the stack shown in FIG. 3.

In FIGS. 3 and 4, the flame 28 in burner 2 is seen to be surrounded by a double-wall stack 27, one longitudinal side of which contains openings for the passage of outer air 31, said openings being in the lower part of outer wall 29 and in the upper part of inner wall 30. The air-fuel mixture from regulator 5 is mixed at 3 with atomized dilute sample solution and supplies a central burner pipe 2', for flame combustion. Through openings in walls 29 and 30, and via the annular space between pipe 2' and wall 33, the outer air 31 necessary for afterburning is fed, preheated and in laminar flow, to the flame 28, the upper part of the flame 28 being at the same time supported by this air. It is found that the described stack configuration prevents cold air from being drawn-in from above the stack (and the flame thereby collapsing). The flame 28 therefore burns uniformly and without flickering, so that variations in measured values caused by the flame itself are minimized.

Openings for the passage of the emission radiation are provided in that longitudinal side of the double-walled stack 27 which is not provided with air passage openings. FIG. 3 shows one such opening 34 in the two walls 32, 33. The angle between the measurement radiation and the radiation passing through the flame is determined by the opening in the two walls 32 and 33; at the same time, longitudinal placement of the wall opening for observing emission radiation of a particular element is selected in accordance with a determination of the longitudinal section of the flame at which the specific observed element burns most quietly. It is the radiation from this section of the flame that is measured.

The new device can be used not only for the measurement of the four elements which have been mentioned by way of example, but it is furthermore also possible, by means of the new device, to measure the lithium content in serum, as is necessary for certain diagnoses.

What is claimed is:

1. Apparatus for the simultaneous photometric determination of a plurality of elements in a liquid sample in which each of the elements to be determined has a receiver associated with it and the signals supplied by said receivers are evaluated via a computer, characterized by the combination of the following elements:
   (a) at least one hollow-cathode lamp (1) whose light contains at least one narrow-band emission line of one of the elements to be determined;
   (b) a burner (2) for producing an elongated flame (28) to which the diluted liquid sample is fed via an atomizer (3);
   (c) photoelectric receivers (12, 13) arranged laterally of the flame (28) for measurement in emission;
   (d) photoelectric receivers (8, 10) arranged behind the flame (28) for measuring the radiation of the hollow-cathode lamp (1) which penetrates the flame (28) in longitudinal direction;
   (e) narrow-band filters (7, 9, 14, 15) arranged in front of each receiver (8, 10, 12, 13) for the passage of a line characteristic of the specific element to be determined;
   (f) an arrangement (16) for the electronic removal of dust flashes in the flame, said dust-flash removal arrangement being connected to said photoelectric receivers (12, 13) arranged laterally of the flame (28);
   (g) said burner including a double-wall stack (27) which surrounds the elongated flame (28), one side of which contains openings for the passage of the outer air in the lower part of the outer wall (29) and in the upper part of the inner wall (30).

2. An apparatus according to claim 1, characterized by the fact that the liquid sample is highly diluted, preferably in the range of 1:50.

3. An apparatus according to claim 1, characterized by the fact that an automatic flow regulator (5) for the fuel gas is provided.

4. An apparatus according to claim 1, characterized by the fact that the filters (7, 9, 14, 15) which are associated with the photoelectric receivers (8, 10, 12, 13) are developed as interference filters.

5. An apparatus according to claim 1, characterized by the fact that the arrangement for the electronic removal of dust flashes contains an operational amplifier (21) whose one input is connected to an input voltage (18) via an RC member (19, 20) while its other input is connected thereto via a resistance divider (22, 23), that is comparator (25) is present whose one input is connected with the output (24) of the operational amplifier (21) and whose other input is connected with the capacitor (19) of the RC member (19, 20), and that to the output of the comparator (25) there is connected a switch (26) which, upon a difference in voltage between the comparator inputs, connects the capacitor (19) directly with the output (24) of the operational amplifier.

6. An apparatus according to claim 5, characterized by the fact that a bias voltage corresponding approximately to the noise level is present on the comparator (25).

7. An apparatus according to claim 1, characterized by the fact that the openings in the double-wall stack (27) are arranged on one longitudinal side (29, 30).

8. An apparatus according to claim 7, characterized by the fact that the other longitudinal side (32, 33) of the double-wall stack (27) is provided with cutouts (34) for the passage of the emission radiation, said cutouts being located at a height at which the specific element to be measured burns quietly in the flame (28).

9. An apparatus according to any one of the preceding claims, taken in the alternative, characterized by its use for the simultaneous measurement of sodium and potassium in emission as well as calcium and magnesium in atomic absorption in body liquids.

10. Apparatus for the simultaneous photometric determination of a plurality of elements in a liquid sample, in which a separate photoelectric receiver is provided for each of the elements to be determined, and in which the electric signal outputs of said receivers are supplied to a computer for evaluation, said apparatus comprising:
  (a) at least one hollow-cathode lamp whose light contains at least one narrow-band emission line of one of the elements to be determined;
  (b) a burner for producing an elongated flame in the path of light emitted by said lamp, and means including an atomizer for feeding mixed fuel and air and diluted liquid sample to said burner;
  (c) one or more of the photoelectric receivers being positioned laterally of the flame for emission measurement unique to one or more elements other than the element having the emission line produced by said lamp;
  (d) an additional one or more of the photoelectric receivers being positioned behind the flame for measurement of light longitudinally penetrating the flame and unique at least to the element having the emission line produced by said lamp;
  (e) a separate narrow-band filter in front of each receiver for limiting each receiver response to the line characteristic of the specific element to which the particular receiver is to respond;
  (f) means for the electronic removal of dust flashes in the flame, said dust-flash removal arrangement being connected to the output of such photoelectric receivers as are positioned laterally of the flame;
  (g) said burner including a double-wall stack surrounding the elongated flame, said stack having a continuous inner wall in the vicinity of the lower part of the flame for preheating a flow of afterburning air, and the inner wall of said stack having openings in the region of the upper part of the flame for supplying said flow as preheated air in said region.

* * * * *